(12) United States Patent
Baecke et al.

(10) Patent No.: US 8,985,115 B2
(45) Date of Patent: Mar. 24, 2015

(54) BUTTERFLY NASAL INTERFACE

(75) Inventors: Martin Baecke, Dessau-Roßlau (DE); Marcel Borgward, Oedheim (DE)

(73) Assignee: inSleep Technologies, LLC, Weston, FL (US)

( * ) Notice: Subject to any disclaimer, the term of this patent is extended or adjusted under 35 U.S.C. 154(b) by 275 days.

(21) Appl. No.: 13/280,650

(22) Filed: Oct. 25, 2011

(65) Prior Publication Data

US 2012/0266890 A1 Oct. 25, 2012

Related U.S. Application Data

(60) Provisional application No. 61/406,315, filed on Oct. 25, 2010.

(51) Int. Cl.
*A61M 16/06* (2006.01)
*A61M 16/08* (2006.01)
*A61M 16/12* (2006.01)
*A61M 16/00* (2006.01)

(52) U.S. Cl.
CPC .......... *A61M 16/06* (2013.01); *A61M 16/0605* (2013.01); *A61M 16/08* (2013.01); *A61M 2016/0661* (2013.01); *A61M 16/0057* (2013.01); *A61M 16/0666* (2013.01); *A61M 16/0683* (2013.01); *A61M 2016/0027* (2013.01); *A61M 2202/0208* (2013.01); *A61M 16/0858* (2013.01); *A61M 16/125* (2013.01); *A61M 16/0611* (2013.01)
USPC .................................................... 128/207.13

(58) Field of Classification Search
CPC .......... A61M 16/06–16/0622; A61M 16/0666–16/0677; A61M 2016/06–2016/0661; A62B 18/08

USPC .......... 128/206.21–207.13, 207.18
See application file for complete search history.

(56) References Cited

U.S. PATENT DOCUMENTS

| 2005/0205096 | A1* | 9/2005 | Matula et al. | 128/207.11 |
| 2008/0053446 | A1* | 3/2008 | Sleeper et al. | 128/205.25 |
| 2008/0289633 | A1 | 11/2008 | Kwok et al. | |
| 2009/0014008 | A1* | 1/2009 | Takishita et al. | 128/207.11 |
| 2009/0095298 | A1* | 4/2009 | Gunaratnam et al. | 128/204.18 |
| 2009/0145429 | A1 | 6/2009 | Ging et al. | |
| 2010/0282265 | A1* | 11/2010 | Melidis et al. | 128/206.26 |
| 2010/0319700 | A1* | 12/2010 | Ng et al. | 128/206.28 |
| 2012/0067349 | A1* | 3/2012 | Barlow et al. | 128/205.25 |

FOREIGN PATENT DOCUMENTS

| WO | 2004/096332 A1 | 11/2004 |
| WO | 2010/139014 A1 | 12/2010 |

OTHER PUBLICATIONS

International Search Report and Written Opinion for PCT/EP2011/068685 mailed Feb. 29, 2012.
International Preliminary Report on Patentability for PCT/EP2011/068685 mailed May 10, 2013.

* cited by examiner

*Primary Examiner* — Rachel Young
(74) *Attorney, Agent, or Firm* — Kevin P. Crosby; GrayRobinson, P.A.

(57) ABSTRACT

A nasal interface including a hard base and a soft pad portion with angled butterfly wing portions. The soft pad portion is connected to the hard base portion, and in some arrangements, can be removed from the hard base portion. The soft pad portion includes a bellows positioned between a lower boarder and the butterfly wings.

20 Claims, 7 Drawing Sheets

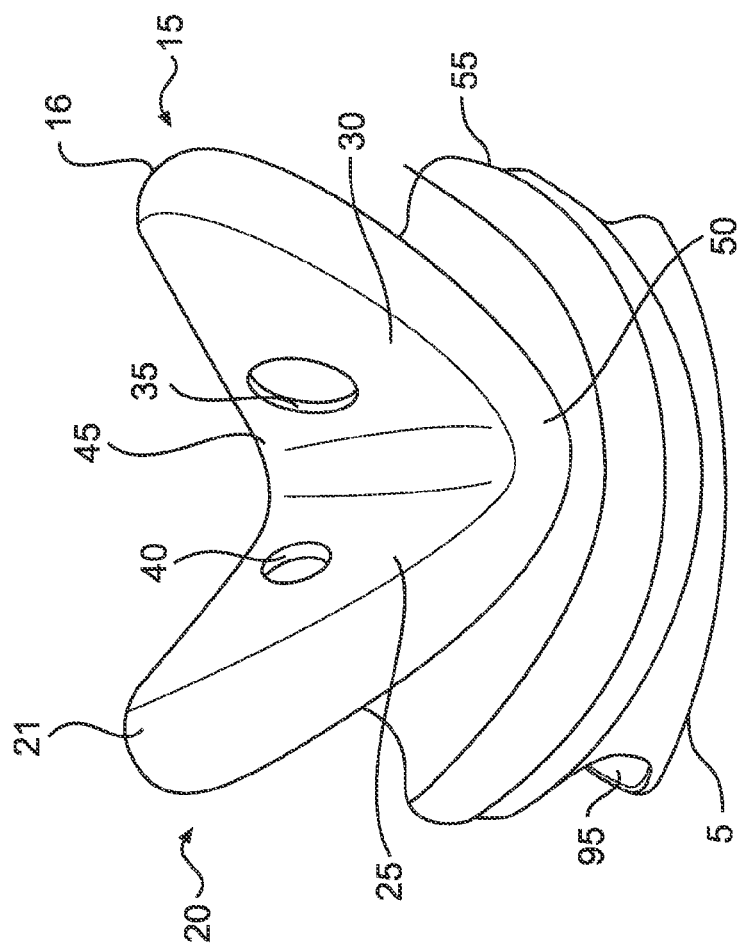
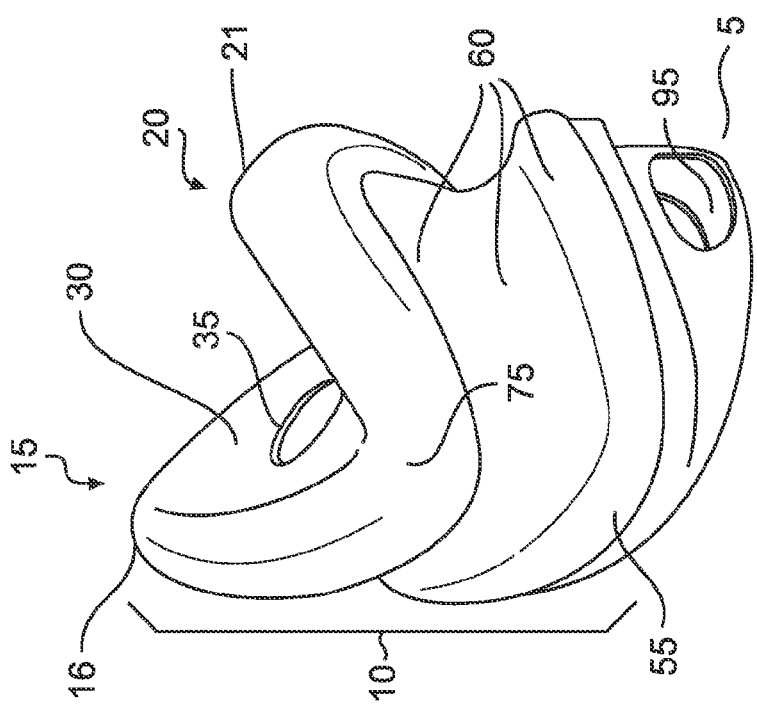

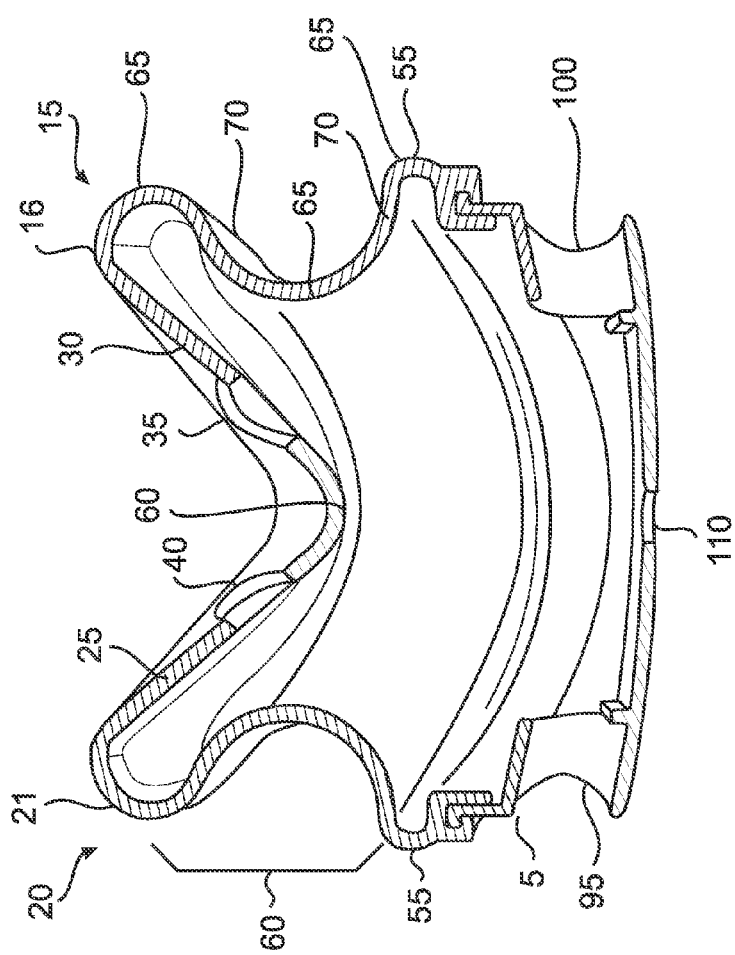
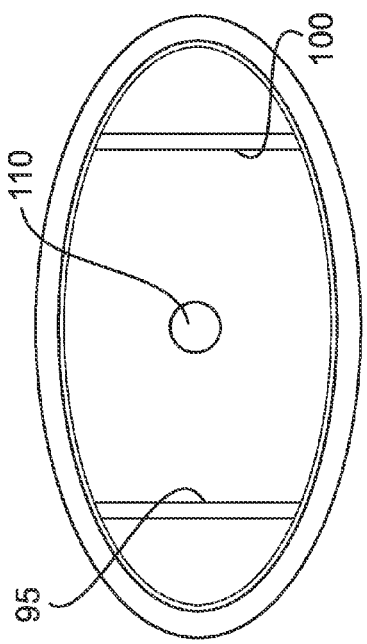

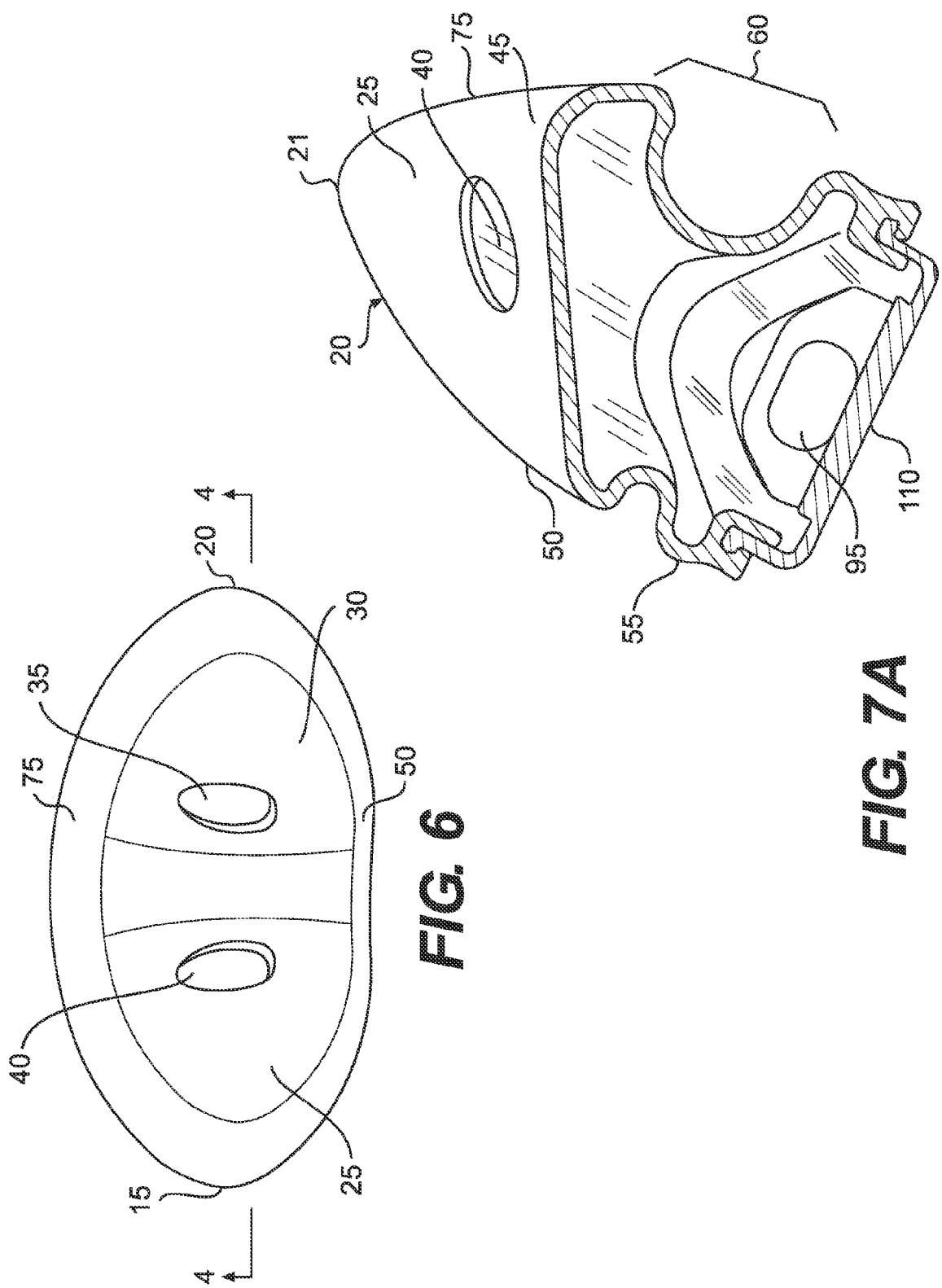

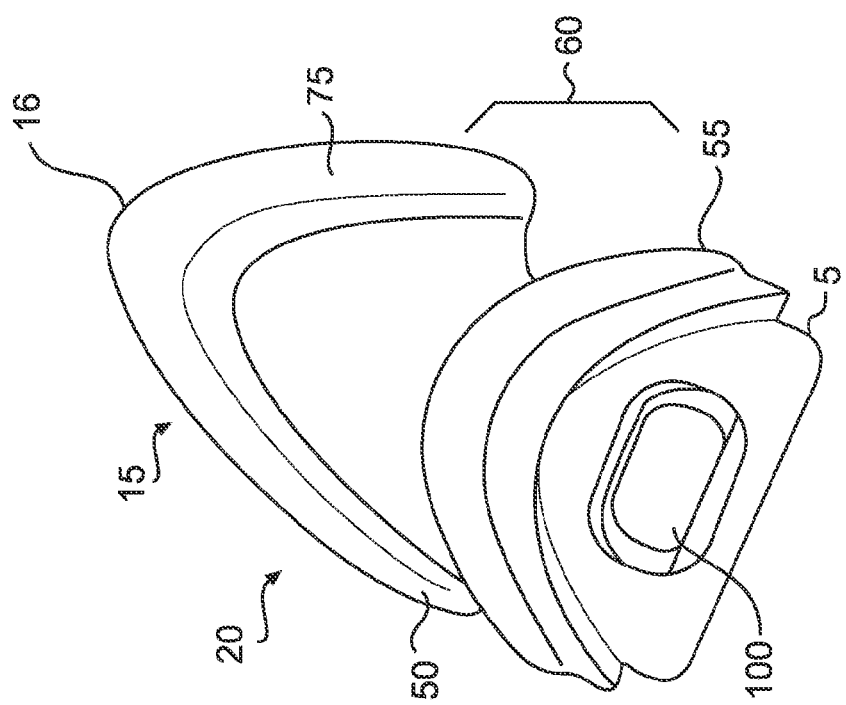

BUTTERFLY NASAL INTERFACE

CROSS-REFERENCE TO RELATED APPLICATIONS

This application claims the benefit of U.S. provisional patent application Ser. No. 61/406,315, entitled Nasal Interface, filed on Oct. 25, 2010, the entire disclosure of which is incorporated herein by reference.

TECHNICAL FIELD

The present disclosure generally relates to a breathing apparatus, and more particularly to a nasal interface for a breathing apparatus that may be used in connection with reducing snoring.

BACKGROUND OF THE DISCLOSURE

Snoring is an affliction that affects many people. Snoring may be an ongoing, regular problem, or may occur intermittently or occasionally. Snoring may result in various problems, both to the person snoring as well as those around the person snoring. For example, snoring has been linked to sleep deprivation, in which the sleeping patterns of the person snoring may be disrupted. Such sleep deprivation may result in daytime drowsiness, lack of focus, as well as other problems. There are a number of other breathing disorders including, but not limited to, OSA, COPD, and Asthma that could be aided by the use of a supplemental breathing apparatus.

FIG. 1 is a schematic view of a general system that can employ a nasal interface in accordance with the present disclosure. Generally, an apparatus for treating snoring can included an air source 1, a nasal interface 3 and a connection 2, such as tubing, connecting the air source 1 and the nasal interface 3. The comfort of a user is important in the arrangement of a nasal interface. It is also important to try to minimize the amount of air flow that leaks out of the nasal interface. In other words, it is desirable to have an efficient coupling between the nasal interface the user's nose so as to try to maximize the amount of air that is transferred between the nasal interface and the user's nose.

SUMMARY OF THE DISCLOSURE

According to a first implementation, a nasal interface can comprise a base portion having a least one inlet; a soft pad portion, including a lower border operatively connected to the base portion, butterfly wing portions positioned at an angle relative to each other and having at least one hole formed therein, and a bellows portion connecting the lower border and the butterfly wing portions.

The details of one or more implementations are set forth in the accompanying drawings and the description below. Other features will become apparent from the description, the drawings, and the claims.

BRIEF DESCRIPTION OF THE DRAWINGS

FIG. 2 is a right rear perspective view of an illustrative embodiment of the present disclosure.

FIG. 3 is a front elevational view of the illustrative embodiment of the present disclosure shown in FIG. 2.

FIG. 4 is a cross sectional front elevational view of the illustrative embodiment show in FIGS. 2 and 3 taken along lines 4-4 of FIG. 6.

FIG. 5 is a top plan view of the base portion 5 in accordance with an embodiment of the disclosure.

FIG. 6 is a top plan view of a soft pad portion of a nasal interface in accordance with the present disclosure.

FIG. 7A is a cross sectional left side elevational view of a nasal interface in accordance with the present disclosure taken along lines 7A-7A of FIG. 6.

FIG. 7B is a left side elevational view of a nasal interface in accordance with the present disclosure.

DETAILED DESCRIPTION OF PREFERRED EMBODIMENTS

Figure 8:
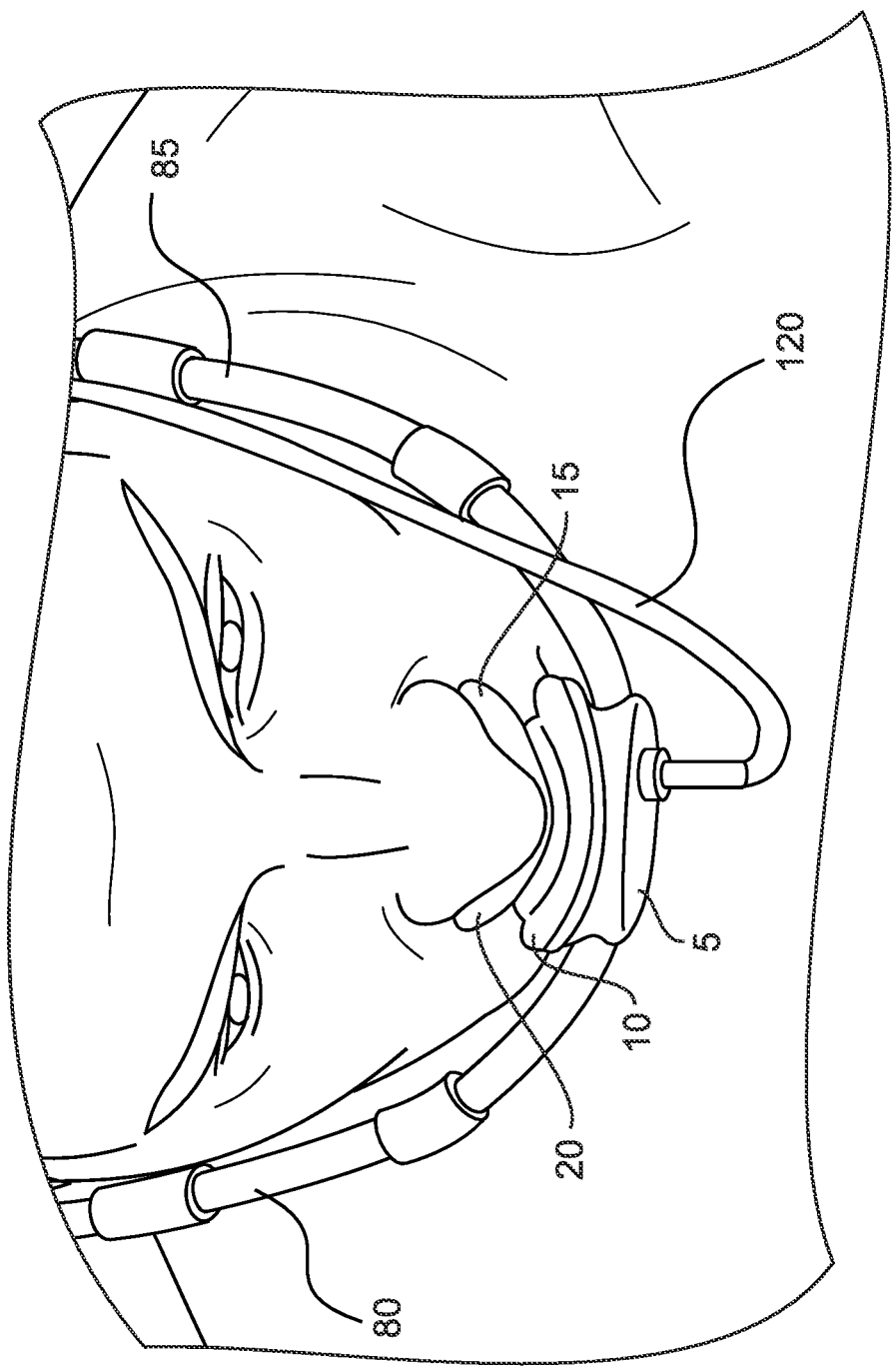
FIG. 8 illustrates a user wearing a nasal interface in accordance with the present disclosure.

FIG. 2 is a perspective view of an illustrative embodiment of the present disclosure. FIG. 3 is a front view of the illustrative embodiment of the present disclosure shown in FIG. 2. Referring to FIGS. 2 and 3, the illustrative exemplary embodiment includes a hard base portion 5 and a soft pad portion 10. The soft pad 10 can comprise a silicon pad, and the base portion 5 can be relatively harder than the soft pad portion 10. As illustrated in FIGS. 2 and 3, the soft pad portion 10 includes a butterfly shaped structure with butterfly wings 15 and 20. The butterfly wings 15 and 20 respectively include upper surfaces 25 and 30 with respective distal ends 16 and 21. The butterfly wings 15 and 20 respectively include therein air holes 35 and 40. These air holes are sized and positioned on the upper surfaces 25 and 30 of butterfly wings 15 and 20 to locate the air holes in registry with a user's nostrils. An example of one such arrangement is shown in FIG. 8. As seen in FIG. 8, the upper surfaces 25 and 30 of the butterfly wings 15 and 20 engage the underside of a user's nose. As also described below, this allows air from the butterfly nasal interface to flow to the user's nostrils. In other embodiments, the upper surfaces 25 and 30 could include protrusions or other physically noticeable features about or near the air holes 35 and 40 to aid in positioning of the nasal interface with respect to a user's nostrils.

In an illustrative embodiment, the upper surfaces 25 and 30 may be positioned relative to each other at an angle of about 90° on the butterfly wings 15 and 20 of a nasal interface in accordance with the present disclosure. An exemplary vertex of a 90° angle corresponding to the included angle between the butterfly wings 15 and 20 is indicated by line 60 in FIG. 4. The selection of the angle is based upon ergonomic studies. Of course, in various embodiments the included angle may vary from about a 180° included angle to about a 45° included angle. The upper surfaces 25 and 30 may seal around the users nostrils as shown in FIG. 8. The upper surfaces 25 and 30 may be pressed smoothly against the user's nose by the systems pressure (e.g., mechanical pressure of the nasal interface as held against the user's nostrils as shown in FIG. 8) to form this seal.

Figure 9:
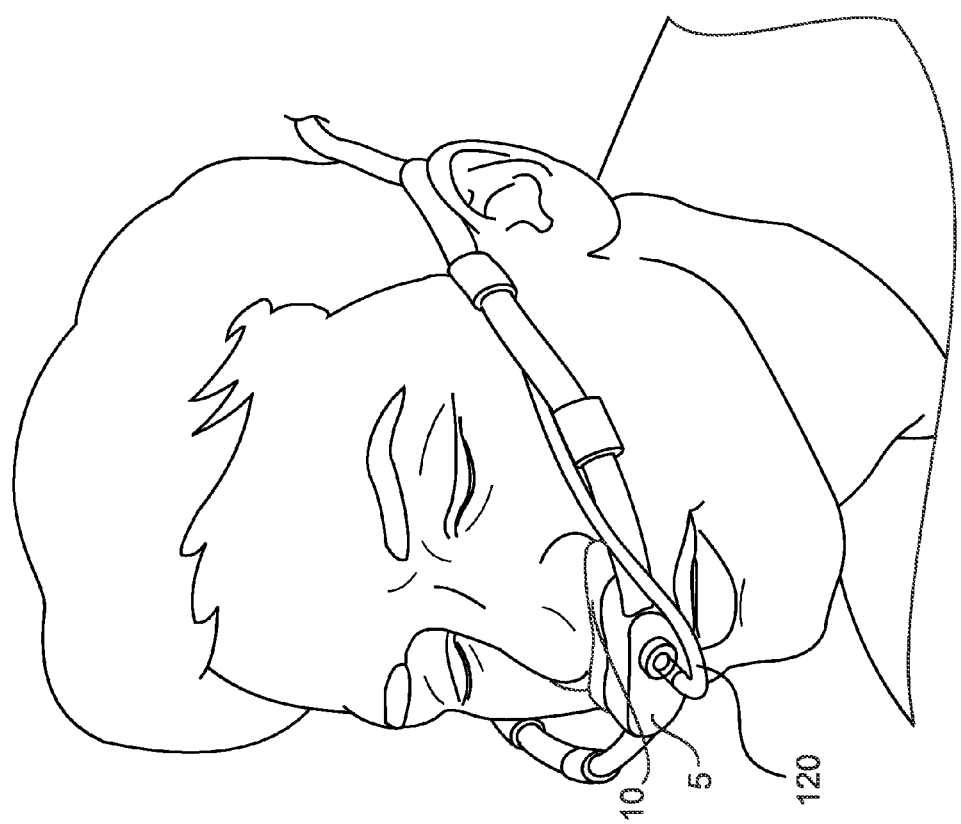
FIG. 9 illustrates a user wearing a nasal interface in accordance with the present disclosure.

Referring to FIG. 2, the upper surfaces 25 and 30 of butterfly wings 15 and 20 slope from a relatively higher position at point 45 to a relatively lower position at point 50. While not necessary to practicing the invention, this slope allows a nasal interface in accordance with the present disclosure to be positioned on a user's nose to conveniently accept tubing such as shown in FIGS. 8 and 9.

Referring to FIGS. 2 and 3, the soft pad portion 10 includes a lower border 55. In the illustrative embodiment, the lower border 55 aids in coupling the soft pad portion 10 to the base portion 5. The coupling can be any convenient coupling, such as a mechanical connection, an adhesive, welding, etc. In some embodiments, the lower border 55 may have a more or less round or oval cross section. The lower border 55 may be tensioned over an upper border of the base portion 10, which can be formed to fit using, for example, a key-lock type connection. The round shape may facilitate a tight sealing between the base and the soft pad 10 because of the tensile forces working radially toward the center. Depending upon the use of the nasal interface and the type of coupling, the base portion 5 can be removable from the soft pad portion 10. Such removal facilitates cleaning the nasal interface or changing one of the base portion 5 or the soft pad portion 10.

FIG. 4 is a cross sectional view of the illustrative embodiment show in FIGS. 2 and 3. In the illustrative embodiment shown in FIG. 4, the soft pad portion 10 includes a bellows 60. Bellows 60 may provide flexibility in height of the nasal interface and the angle at which the upper surfaces 25 and 30 reside with respect to a user's nostrils. The bellows 60 can function as a spring if there is pressure between the user's nose and the base portion 5.

The illustrated bellows includes vertical parts 65 (e.g., relative to the base) and horizontal parts 70 (e.g., relative to the base). The vertical parts 65 may give stability to the shape. The horizontal parts may allow a vertical movement of upper surfaces 25 and 30. This vertical movement may be for the whole soft pad portion 10, relative to the base portion 5. The vertical movement may be on one side of the pad, or both sides of the pad (including movement to different degrees on different sides). Thus, the bellows 60 allows the angle of the upper surfaces 25 and 30 relative to the base to change. This flexibility of the bellows and ability for the angle of the upper surfaces 25 and 30 to change may result in a self sealing effect between a user's nostrils and the upper surfaces 25 and 30. While illustrated as extending around the nasal interface, the bellows 60 may extend only around a portion of the nasal interface.

FIG. 6 is a partial top view of a soft pad portion 10 of a nasal interface in accordance with the present disclosure. The holes 35 and 40 in the upper surfaces 25 and 30 let the air into and out of a user's nostrils. The size and shape of these holes can be adjusted depending upon the desired flow and acoustic characteristics of a given design in accordance with the disclosure. While not shown in FIG. 6, the holes may have a cross section optimized for low pressure losses and low noise from the airflow through the holes. Also, in the illustrated embodiment, the holes 35 and 40 are near the edges between upper surfaces 25 and 30, and side surface 75. This position is shown in the illustrative embodiment because most people have nostrils beginning very near or directly above the user's upper lips.

Because a user's nostrils can begin directly from the upper lips there may not be a significant surface to seal the upper surfaces 25 and 30 to the user's nose. To address this, an illustrative embodiment may include side surface 75. The side surface 75 can aid in providing a seal between the nasal interface and the user. It can do so by the side surface 75 abutting and pressing against the user's upper lip.

The nasal interface, as shown in FIG. 9, may be positioned at an angle against the nose and upper lip of a user. In such an embodiment, the surfaces of the soft pad portion 10 have very soft and safe position. Because of the flexibility of the soft pad 10, such as provided by the bellows 60, the nasal interface can be adjusted relative to three planes: with respect to upper lips, and the two butterfly wings 15 and 20 with respect to a user's nostrils. This flexibility in positioning allows the position of the nasal interface to be highly defined. Gliding of the nasal interface may be reduced and/or prevented by this structural form. In addition tilting of the base portion 5 may prevent leakage due to the spring like function of the bellows 60 and the pressure the bellows 60 provides against a user's nose and the flexibility in angle of the upper surfaces 25 and 30 that the bellows 60 permits. Very low forces are needed with embodiments in accordance with the disclosure to effectively seal the nasal interface with a user's nostrils.

In the illustrated embodiment, the base portion 5 can be connected (e.g., glued, welded, snap or press fit, etc.) with one or more tubes as shown in FIG. 8. The illustrative embodiment shown in FIG. 8 utilizes two tubes 80 and 85, rather than one tube. The tubes connect to holes 95, 100 in the base portion 5.

The holes 95, 100 can be oriented in different angles. In one embodiment, the holes 95, 100 can be adjusted in every direction that is reasonable to guarantee a perfect seat of the nasal interface. While the illustrated embodiments depict two holes 95 and 100 for connecting to two tubes 80 and 85 on either side of the nasal interface, other arrangements may also be utilized. For example, one or more tubes may be connected at various locations on the nasal interface, such as the front of the nasal interface, or other suitable location.

The tubes 80, 85, in addition to supplying air to the nasal interface, may be utilized for holding the mask in the right position for maintaining connection to (e.g., sealing engagement with) the user's nose. In one embodiment, the tubes may come from a direction above the user's ear such as shown in FIG. 9. In other embodiments, a headgear arrangement not including the tubes (and/or in addition to the tubes) may be utilized for positioning the mask relative to the user.

Figure 1:
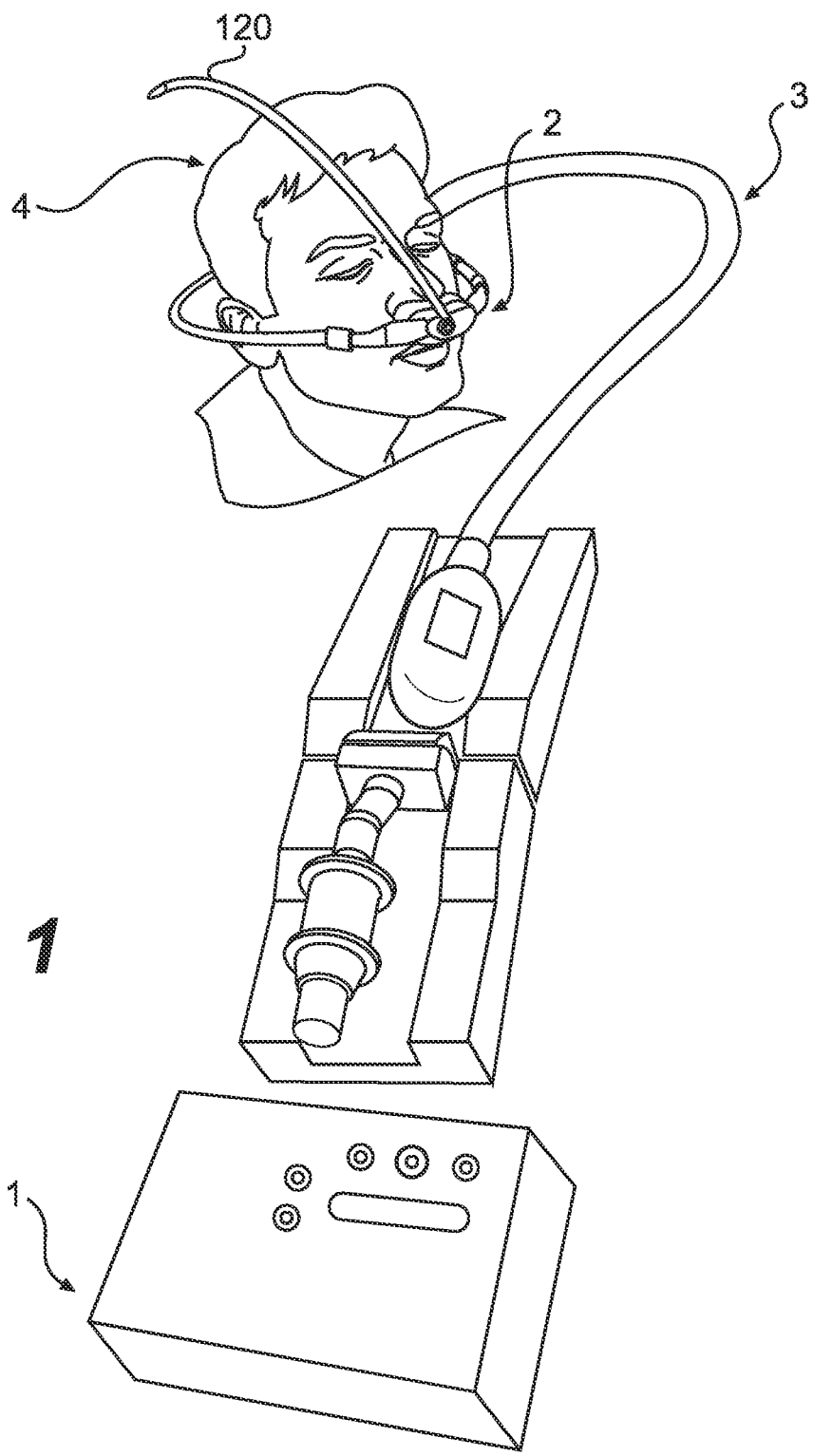
FIG. 1 is a schematic view of a general system that can employ a nasal interface in accordance with the present disclosure.

Referring to FIGS. 4 and 5, the base portion 5 may have an additional hole 110. The size and shape of the hole 110 can be selected in accordance with the flow and acoustic characteristics of a given design in accordance with the disclosure. FIG. 5 illustrates a top view of the base portion 5 in accordance with an embodiment of the disclosure. The additional hole 110 can be, as shown in the illustrative embodiments, open to the environment (air outlet). In one embodiment, the hole 110 may be designed to allow airflow of about 20 l/min at 2 mbar overpressure inside the mask. This may reduce and/or prevent a $CO_2$-concentration to the user from being too high. Additionally, the hole 110 may be sized to provide an open breathing interface, such that the user may generally breathe ambient air entering through the hole. The ambient air may be supplemented with gasses (e.g., oxygen, etc.) supplied via the tube(s) (e.g., tubes 80, 85). As shown in FIGS. 8 and 9, an additional tube 120 can be used to measure the pressure within the nasal interface. It can also be used for pressure feedback to the air supply 1 shown in FIG. 1.

FIG. 7A is a cross section view of a nasal interface in accordance with the present disclosure, viewed from the left side. FIG. 7B is a left side view of a nasal interface in accordance with the present disclosure. These views of an illustrative embodiment in accordance with the disclosure provide further illustration of the flexibility that the disclosed structure provides. FIG. 7A also illustrates the slope of the upper surface 25, as mentioned above.

For a nasal interface which fits a wide range of users, the nasal interface can have a relatively small dimension with respect to users' noses. In addition, the shape of the butterfly wings 25, 30, might be bigger depending upon the target size nose of users. As seen in FIGS. 2, 3, and 5, the base portion 5 has a relatively small dimension. The inner cross section, such as shown in FIG. 5, allows its overall shape to be selected for styling. The structure of the disclosed illustrative embodiments allows the base portion 5 to move sideward and upwards with reduced displacement of butterfly wings 25, 30 at the user's nose.

Having thus described the invention of the present application in detail and by reference to embodiments thereof, it will be apparent that modifications and variations are possible without departing from the scope of the invention defined in the appended claims.

What is claimed is:

1. A nasal interface comprising:
a base portion having a least one airflow inlet;
a soft pad portion, including:
a lower border operatively connected to the base portion,
a pair of wing members positioned at an angle relative to each other, each wing member having at least one airflow aperture formed therein, each of the wing members being at least partially comprised of a hollow bladder fluidly communicating the at least one inlet with the at least one airflow aperture,
each wing member comprised of a substantially flat upper wall adapted to be placed in sealing contact with the underside of a user's nose, each upper wall being devoid of any protrusions adapted to enter the user's nostrils, each wing member also including a depending wall connecting the upper wall with the lower border, each upper wall having an end farthest from their respective at least one airflow aperture that is directly contiguous with their respective depending wall.

2. The nasal interface according to claim 1, wherein the base portion further includes an airflow outlet.

3. The nasal interface according to claim 1, further including a bellows portion defined by the depending wall which includes at least two horizontal wall sections and at least one vertical wall section positioned between the at least two horizontal wall sections.

4. The nasal interface according to claim 3, wherein the horizontal wall sections and the vertical wall section are at least partially curved.

5. The nasal interface according to claim 1, wherein each wing member terminates in a respective distal end, and each upper wall slopes in a direction transverse to a line between the distal ends.

6. The nasal interface according to claim 5, wherein the angle between the wing members is in the range of approximately 45° to approximately 180°.

7. A nasal interface for unobtrusively sealing against an underside of a user's nose, comprising;
a base adapted to be connected to a supply of pressurized air;
a nasal pad adapted to be connected to the base, the nasal pad comprising a lower border adapted to mate with the base, the nasal pad further including left and right wing members adapted to be placed adjacent to respective left and right sides of an underside of a user's nose;
the left and right wing members including respective left and right nose contacting webs, the left web defining a left airflow aperture and the right web defining a right airflow aperture separate from the left airflow aperture, and each web adapted to be placed in sealing contact with respective left and right sides of an underside of a user's nose;
each web being substantially flat and being devoid of any protrusions adapted to enter the user's nostrils, each wing member also including a depending wall connecting the upper wall with the lower border;
each of the left and right wing members defining a hollow interior adapted to fluidly communicate the supply of pressurized air to of the user's nostrils;
each web having an end farthest from their respective airflow aperture that is directly contiguous with their respective depending wall.

8. The nasal interface of claim 7, further comprising a bellows section interposed between the left and right webs and the lower border to permit movement of the webs relative to the base.

9. The nasal interface according to claim 7, wherein the base further includes an airflow outlet.

10. The nasal interface according to claim 8, wherein the bellows section includes at least two horizontal wall sections and at least one vertical wall section positioned between the at least two horizontal wall sections.

11. The nasal interface according to claim 10, wherein the horizontal wall sections and the vertical wall section are at least partially curved.

12. The nasal interface according to claim 7, wherein each wing member terminates in a respective distal end, and each web slopes in a direction transverse to a line between the distal ends.

13. The nasal interface according to claim 10, wherein the angle between the webs is in the range of approximately 45° to approximately 180°.

14. A nasal interface for delivering a supply of air to a user, comprising:
a base adapted to be fluidly connected to a supply of pressurized air;
a nasal pad comprised of left and right wing members adapted to be placed in sealing contact with respective left and right sides of an underside of the user's nose, the nasal pad further comprised of a lower border adapted to sealingly engage the base;
each wing member defining a substantially flat nose-engaging web each of which in turn defines an airflow aperture such that there are at least two separate airflow apertures at a proximal end of the pad; and
each web being devoid of any protrusions adapted to enter the user's nostrils, each wing member also including a depending wall connecting the nose-engaging web with the lower border;
each of the left and right wing members defining a hollow interior adapted to fluidly communicate the supply of pressurized air to the user's nostrils through the respective airflow aperture;
each web having an end farthest from their respective airflow aperture that is directly contiguous with their respective depending wall.

15. The nasal interface of claim 14, further comprising a bellows section interposed between each nose-engaging web and the lower border to permit movement of the webs relative to the base.

16. The nasal interface according to claim 14, wherein the base further includes an airflow outlet.

17. The nasal interface according to claim 15, wherein the bellows section includes at least two horizontal wall sections and at least one vertical wall section positioned between the at least two horizontal wall sections.

18. The nasal interface according to claim 17, wherein the horizontal wall sections and the vertical wall section are at least partially curved.

19. The nasal interface according to claim 14, wherein each wing member terminates in a respective distal end, and each web slopes in a direction transverse to a line between the distal ends.

20. The nasal interface according to claim 17, wherein the angle between the webs is in the range of approximately 45° to approximately 180°.

* * * * *